United States Patent
Pham et al.

(10) Patent No.: US 6,673,264 B2
(45) Date of Patent: Jan. 6, 2004

(54) AZEOTROPE-LIKE COMPOSITIONS OF 1,1,1,3,3-PENTAFLUOROBUTANE AND HYDROGEN FLUORIDE

(75) Inventors: Hang T. Pham, Amherst, NJ (US); Rajiv R. Singh, Getzville, NY (US); Hsueh S. Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/160,673

(22) Filed: Jun. 3, 2002

(65) Prior Publication Data

US 2003/0009065 A1 Jan. 9, 2003

Related U.S. Application Data

(60) Provisional application No. 60/295,049, filed on Jun. 1, 2001.

(51) Int. Cl.$^7$ ................................................. C09K 3/00
(52) U.S. Cl. .................. 252/182.15; 252/580; 570/161; 570/164; 570/165; 570/134; 570/177; 570/178; 570/180; 203/77; 203/80
(58) Field of Search ............................ 252/182.15, 580; 570/161, 178, 177, 180, 164, 165, 134; 203/77, 80

(56) References Cited

U.S. PATENT DOCUMENTS

| | | | |
|---|---|---|---|
| 4,950,364 A | 8/1990 | Wismer | 203/50 |
| 5,208,398 A | 5/1993 | Wismer | 570/177 |
| 5,395,997 A | 3/1995 | Van Der Puy et al. | 570/167 |
| 5,917,098 A | 6/1999 | Bertocchio et al. | 570/164 |
| 5,918,481 A | 7/1999 | Pham et al. | 62/631 |
| 6,399,841 B1 * | 6/2002 | Lambert et al. | 570/180 |

FOREIGN PATENT DOCUMENTS

WO  WO 00/56687  * 9/2000

* cited by examiner

*Primary Examiner*—Johann Richter
*Assistant Examiner*—Elvis O. Price
(74) *Attorney, Agent, or Firm*—Colleen D. Szuch; Deborah M. Chess

(57) ABSTRACT

The invention relates to azeotropic and azeotrope-like mixtures of 1,1,1,3,3-pentafluorobutane (HFC-365) and hydrogen fluoride and a process for separating the azeotrope-like mixtures. The compositions of the invention are useful as an intermediate in the production of HFC-365. The latter is useful as a nontoxic, zero ozone depleting fluorocarbon useful as a solvent, blowing agent, refrigerant, cleaning agent and aerosol to propellant.

2 Claims, No Drawings

AZEOTROPE-LIKE COMPOSITIONS OF 1,1,1,3,3-PENTAFLUOROBUTANE AND HYDROGEN FLUORIDE

CROSS-REFERENCE TO RELATED APPLICATION

This application claims priority to provisional application Ser. No. 60/295,049, which was filed with the United States Patent and Trademark Office on Jun. 1, 2001 and is incorporated herein by reference.

FIELD OF THE INVENTION

The present invention relates to azeotropic and azeotrope-like compositions of 1,1,1,3,3-pentafluorobutane (HFC-365) and hydrogen fluoride.

BACKGROUND

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, it is desirable to use fluids having low or even zero ozone depletion potential, such as hydrofluorocarbons ("HFC's"). Thus, the use of fluids that do not contain chlorofluorocarbons ("CFCs") or hydrochlorofluorocarbons ("HCFCs") is desirable. Additionally, the use of single component fluids or azeotropic mixtures, which do not fractionate on boiling and evaporation, is desirable. However, the identification of new, environmentally-safe, non-fractionating mixtures is complicated due to the fact that azeotrope formation is not readily predictable.

The industry is continually seeking new fluorocarbon based mixtures that offer alternatives to, and are considered environmentally safer substitutes for, CFC's and HCFCs. Of particular interest are combinations or mixtures containing 1,1,1,3,3-pentafluorobutane (HFC-365) and an acid, both having low ozone depletion potentials. (HFC-365 is well known in the art and is described in U.S. Pat. Nos. 5,917,098; 5,395,997; 4,950,364; and 5,208,398, which are incorporated herein by reference.) Such mixtures are the subject of this invention.

DETAILED DESCRIPTION OF PREFERRED EMBODIMENT

The present inventors have developed several compositions that can help to satisfy the continuing need for substitutes for CFCs and HCFCs. In one embodiment, the present invention provides azeotrope-like compositions comprising 1,1,1,3,3-pentafluorobutane ("HFC-365mfc") and hydrogen fluoride ("HF").

It is known that the composition of an azeotropic mixture varies with pressure variations in that the relative concentrations of the components of the azeotropic mixture will change with pressure. However, the degree to which a particular azeotropic mixture will vary with pressure is unpredictable. Accordingly, it is also unpredictable whether two compounds with close boiling points in azeotropic admixture can be separated by distillation which takes advantage of the pressure variation effect (for example, pressure swing distillation).

Applicants have discovered that the relative concentrations of the components of the 1,1,1,3,3-pentafluorobutane/hydrogen fluoride azeotrope-like composition change to a significant degree, and more than one skilled in the art would expect, as the pressure to which the azeotrope-like composition is exposed is changed. Such a significant composition differential facilitates separation because, in certain preferred embodiments, either 1,1,1,3,3-pentafluorobutane or hydrogen fluoride will concentrate in the distillate during distillation at one pressure, and then, upon distillation of the distillate at a different pressure, will tend to concentrate in the bottoms. This way, the component can be removed from the mixture through the bottoms.

Since these pressures are within the operating parameters of conventional distillation equipment, the process of the present invention can be practiced using existing equipment with little or no modification.

Accordingly, in another embodiment, the present invention provides a process for separating 1,1,1,3,3-pentafluorobutane from an 1,1,1,3,3-pentafluorobutane/hydrogen fluoride azeotropic mixture, which process comprises, consists essentially of, or consists of the steps of:

(A) distilling a mixture comprising an azeotropic mixture of 1,1,1,3,3-pentafluorobutane and hydrogen fluoride at a first pressure to produce a first overhead stream enriched in either 1,1,1,3,3-pentafluorobutane or hydrogen fluoride and a first bottoms stream enriched in the other component; and (B) redistilling the first overhead stream at a second pressure to produce a second overhead stream enriched in the component enriched in the first bottoms stream and a second bottoms stream enriched in the component enriched in the first overhead stream.

The invention also provides a method of forming an azeotropic or azeotrope-like composition which consists essentially of blending 1,1,1,3,3-pentafluorobutane and hydrogen fluoride.

The term "enriched" is used herein to refer to the condition during the distillation of a mixture in which the concentration of one component in either the distillate or a bottoms product is higher relative to its concentration in the mixture.

The invention still further provides a process for removing 1,1,1,3,3-pentafluorobutane from a mixture containing 1,1,1,3,3-pentafluorobutane and at least one impurity, which comprises adding hydrogen fluoride to the mixture in an amount sufficient to form an azeotropic or azeotrope-like composition of the 1,1,1,3,3-pentafluorobutane and the hydrogen fluoride, and thereafter separating the azeotropic composition from the impurity.

Compositions

The present compositions are azeotrope-like compositions. As used herein, the term "azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the state pressure and temperature. In practice, this means that the components of an azeotropic mixture are constant boiling and cannot be separated during a phase change.

Azeotrope-like compositions are constant boiling or essentially constant boiling. In other words, for azeotrope-like compositions, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree. All azeotrope-like compositions of the invention within the indicated ranges as well as certain compositions outside these ranges are azeotrope-like.

The azeotrope-like compositions of the invention may include additional components that do not form new azeotrope-like systems, or additional components that are not in the first distillation cut. The first distillation cut is the first cut taken after the distillation column displays steady state operation under total reflux conditions. One way to determine whether the addition of a component forms a new azeotrope-like system so as to be outside of this invention is to distill a sample of the composition with the component under conditions that would be expected to separate a non-azeotropic mixture into its separate components. If the mixture containing the additional component is non-azeotrope-like, the additional component will fractionate from the azeotrope-like components. If the mixture is azeotrope-like, some finite amount of a first distillation cut will be obtained that contains all of the mixture components that is constant boiling or behaves as a single substance.

It follows from this that another characteristic of azeotrope-like compositions is that there is a range of compositions containing the same components in varying proportions that are azeotrope-like or constant boiling. All such compositions are intended to be covered by the terms "azeotrope-like" and "constant boiling". As an example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

The present invention provides azeotrope and azeotrope-like compositions comprising 1,1,1,3,3-pentafluorobutane and hydrogen fluoride. Preferably, the novel azeotrope-like compositions of the present invention comprise effective amounts of hydrogen fluoride and 1,1,1,3,3-pentafluorobutane. The term "effective amounts" as used herein refers to the amount of each component which upon combination with the other component or components, results in the formation of the present azeotrope-like compositions.

The inventive compositions are preferably binary azeotropes which consist essentially of hydrogen fluoride with 1,1,1,3,3-pentafluorobutane. In the certain embodiments, the inventive compositions consist essentially of from about 1 to about 95 weight percent 1,1,1,3,3-pentafluorobutane and from about 5 to about 99 weight percent hydrogen fluoride, preferably the inventive compositions consist essentially of from about 5 weight percent to about 90 weight percent 1,1,1,3,3-pentafluorobutane and about 10 to about 95 weight percent hydrogen fluoride. In certain more preferred embodiments, the present compositions consist essentially of about 4 weight percent to about 10 weight percent hydrogen fluoride and about 90 to about 96 weight percent 1,1,1,3,3-pentafluorobutane.

The compositions of the present invention have a vapor pressure of about 15 psia to about 22 psia at about 20.2° C. or a vapor pressure of about 29 psia to about 36 psia at about 40.2° C. By way of example, an azeotrope-like composition having about 6.8±3 weight percent hydrogen fluoride and about 73.2±3 weight percent 1,1,1,3,3-pentafluorobutane has been found to have a vapor pressure of about 18.15 psia at about 20.2° C. An azeotrope-like composition having about 6.8±3 weight percent hydrogen fluoride and about 73.2±3 weight percent 1,1,1,3,3-pentafluorobutane has been found to have a vapor pressure of about 32.19 psia at about 40.2° C.

Uses of the Compositions

The compositions of the present invention may be used in a wide variety of applications as substitutes for CFCs and HCFCs. For example, the present compositions are useful as solvents, blowing agents, refrigerants, cleaning agents and aerosols. In addition, the compositions of the present invention are particularly suited for use in producing relatively pure 1,1,1,3,3-pentafluorobutane.

In one embodiment, the present invention provides methods for separating 1,1,1,3,3-pentafluorobutane from an azeotropic mixture of 1,1,1,3,3-pentafluorobutane and hydrogen fluoride, which process comprises the steps of:

(A) distilling a mixture comprising an azeotropic mixture of 1,1,1,3,3-pentafluorobutane and hydrogen fluoride at a first pressure to produce a first overhead stream enriched in either the 1,1,1,3,3-pentafluorobutane or the hydrogen fluoride and a first bottoms stream enriched in the other component; and (B) redistilling the first overhead stream at a second pressure to produce a second overhead stream enriched in the component enriched in the first bottoms stream and a second bottoms stream enriched in the component enriched in the first overhead stream.

Any mixture comprising an azeotropic mixture of 1,1,1,3,3-pentafluorobutane and hydrogen fluoride may be used in the present methods. While such mixtures may be provided via any conventional source, in certain preferred embodiments, the mixtures are supplied as a products stream resulting from a manufacturing process including, for example, the manufacture of fluorocarbons. In such preferred embodiments, the by-products, reactants, and reaction intermediates of the fluorocarbon production process may be present in the mixture along with 1,1,1,3,3-pentafluorobutane and hydrogen fluoride.

The methods of the present invention may be performed using a single distillation column or a series of distillation columns. In embodiments wherein a single distillation column is used, the methods of the present invention are typically performed as batch distillations. The mixture may be fed, for example, into a batch distillation column operating at a first pressure. The distillate is then collected and refed into the column at a second pressure. Preferably, the methods of the present invention are performed using a series of distillation columns, meaning at least two columns, operating at different pressures in a batch or continuous distillation. Examples of distillation columns and methods suitable for use in the present invention are disclosed in U.S. Pat. No. 5,918,481 (issued to AlliedSignal), which is incorporated herein by reference.

Whether the distillation process is continuous or batch, the pressures at which the distillations are conducted preferably are such that conventional distillation apparatus can be used. In preferred embodiments, one distillation pressure is higher than another distillation pressure used. The higher distillation pressure generally may range from about 50 to about 400 psia, preferably about 100 to about 250, more preferably about 150 to 220 psia. The lower distillation pressure generally may range from about 5 psia to about 50 psia, preferably from about 5 psia to less than about 35, more preferably from about 5 psia to less than about 25, and even more preferably from about 5 psia to less than about 20 psia.

The temperatures at which these distillations are performed are directly related to the boiling points and pressures used, and are well within the scope of knowledge of one skilled in the art.

In certain other embodiments, the present invention provides a method for removing 1,1,1,3,3-pentafluorobutane from a mixture containing 1,1,1,3,3-pentafluorobutane and at least one impurity. As used herein, the term "impurity" refers to any compound present in a mixture with 1,1,1,3,3-pentafluorobutane from which it is desirable, for a given application, to separate the 1,1,1,3,3-pentafluorobutane. Preferably, the impurity itself does not form an azeotrope-like mixture with 1,1,1,3,3-pentafluorobutane, hydrogen fluoride or a mixture of 1,1,1,3,3pentafluorobutane and hydrogen fluoride. Typical impurities include other halocarbons which may be miscible with 1,1,1,3,3-pentafluorobutane such as, for example, 1,1,1,3,3-hexachlorobutane (HCC-360).

The method for separating 1,1,1,3,3-pentafluorobutane and at least an impurity comprises adding hydrogen fluoride to the mixture in an amount sufficient to form an azeotrope-like composition of the 1,1,1,3,3-pentafluorobutane and the hydrogen fluoride, and then separating the azeotropic composition from the mixture.

The azeotropic composition of the present method may be separated from the mixture comprising the impurity by any of a number of conventional methods. Examples of separation methods include, for example, distillation, scrubbing, other art-recognized separating means, and combinations of two or more thereof.

Any mixture containing 1,1,1,3,3-pentafluorobutane and at least one impurity may be used in the present method. While such mixtures may be provided via any conventional source, in certain preferred embodiments, the mixtures are reaction products resulting from a manufacturing process, most notably, the production of 1,1,1,3,3-pentafluorobutane.

Those of skill in the art will recognize that the amount of hydrogen fluoride to be added to the mixture, and to form an azeotrope-like composition, will depend on the conditions under which the azeotrope-like composition is formed. In light of the disclosure herein, those of skill in the art will be readily able to determine the amounts of hydrogen fluoride necessary to form azeotrope-like compositions with 1,1,1,3,3-pentafluorobutane under a wide range of pressures and temperatures.

The following non-limiting examples serve to illustrate the invention.

EXAMPLE 1

Binary compositions consisting essentially of 1,1,1,3,3-pentafluorobutane (HFC-365mfc) and hydrogen fluoride are blended to form homogeneous mixtures having different compositions. The vapor pressures of the mixtures were measured at 20.2° C. and 40.2° C.

Table 1 shows the vapor pressure measurement of 1,1,1,3,3-pentafluorobutane and hydrogen fluoride as a function of composition of weight percent hydrogen fluoride at two constant temperatures of 20.2° C. and 40.2° C. From this data it is observed that at 20.2° C. the composition exhibits azeotrope-like properties at about 6.8 weight percent. Based on further observations made during the experiment, it is determined that the composition at which the vapor pressure is the maximum is about 4 weight percent hydrogen fluoride or between about 4 and 8 weight percent hydrogen fluoride at 20.2° C. Based on further observations made during the experiment, it is determined that the composition at which the vapor pressure is the maximum at 40.2° C. is about 8 weight percent hydrogen fluoride or between about 4 and 10 weight percent hydrogen fluoride. From this example it is determined that the azeotropic composition is about 4 weight percent hydrogen fluoride at 20.2° C. and about 8 weight percent hydrogen fluoride at 40.2° C.

TABLE 1

| WEIGHT PERCENT Hydrogen Fluoride (remainder HFC-365 mfc) | PRESSURE (PSIA) | |
| --- | --- | --- |
| | T = 20.2° C. | T = 40.2° C. |
| 0.0 | 15.53 | 29.42 |
| 6.8 | 18.15 | 32.19 |
| 100.0 | 6.65 | 13.98 |

The data also show that the vapor pressure of mixtures of 1,1,1,3,3-pentafluorobutane and hydrogen fluoride is higher, at all indicated blend proportions, than 1,1,1,3,3-pentafluorobutane and hydrogen fluoride alone, i.e. as indicated in the first and last rows when hydrogen fluoride is 0.0 wt. % and 1,1,1,3,3-pentafluorobutane is at 100.0 wt. % as well as when 1,1,1,3,3-pentafluorobutane is at 0.0 wt. % and hydrogen fluoride is at 100.0 wt. %. The shift in composition with temperature or pressure shows that 1,1,1,3,3-pentafluorobutane can be separated from hydrogen fluoride by pressure swing distillation.

What is claimed is:

1. An azeotrope-like composition which consists essentially of from about 90 weight percent to about 96 weight percent 1,1,1,3,3-pentafluorobutane and from about 4 to about 10 weight percent hydrogen fluoride, said composition having a vapor pressure of about 15 psia to about 22 psia at about 20.2° C. or a vapor pressure of above 29 psia to about 36 psia at about 40.2° C.

2. An azeotrope-like composition which consists essentially of from about 90 weight percent to about 96 weight percent 1,1,1,3,3-pentafluorobutane and from about 4 to about 10 weight percent hydrogen fluoride.

* * * * *